(12) United States Patent
Tatemoto

(10) Patent No.: US 6,274,677 B1
(45) Date of Patent: Aug. 14, 2001

(54) PROCESS FOR THE PRODUCING PERFLUOROVINYL ETHERSULFONIC ACID DERIVATIVES AND COPOLYMER OF THE SAME

(75) Inventor: Masayoshi Tatemoto, Settsu (JP)

(73) Assignee: Daikin Industries Ltd., Osaka (JP)

(*) Notice: Subject to any disclaimer, the term of this patent is extended or adjusted under 35 U.S.C. 154(b) by 0 days.

(21) Appl. No.: 09/402,168

(22) PCT Filed: Mar. 31, 1998

(86) PCT No.: PCT/JP98/01472

§ 371 Date: Sep. 30, 1999

§ 102(e) Date: Sep. 30, 1999

(87) PCT Pub. No.: WO98/43952

PCT Pub. Date: Oct. 8, 1998

(30) Foreign Application Priority Data

Mar. 31, 1997 (JP) .................................................. 9-080274

(51) Int. Cl.[7] .............................. C08F 14/18; C08F 16/24
(52) U.S. Cl. ...................... 525/276; 525/200; 525/326.2; 526/247; 526/255
(58) Field of Search ................................. 525/276, 200, 525/326.2; 526/247, 255

(56) References Cited

U.S. PATENT DOCUMENTS 4,804,727 * 2/1989 Ezzell et al. .......................... 526/247

5,981,673 * 11/1999 DeSimone et al. ................... 526/247

FOREIGN PATENT DOCUMENTS

| 57-85367 | 5/1982 | (JP) . |
| 58-500567 | 4/1983 | (JP) . |
| 63-310988 | 12/1988 | (JP) . |
| 5221880 | 5/1993 | (JP) . |

* cited by examiner

Primary Examiner—Nathan M. Nutter
Assistant Examiner—Olga Asinovsky

(57) ABSTRACT

A compound of the formula (1): $FSO_2CFXCF_2O(CFXCF_2O)_nCF—(CF_2Y)COF$ in which X is a fluorine atom, a chlorine atom or a trifluoromethyl group, Y is a fluorine atom, a chlorine atom, a bromine atom or an iodine atom, and n is a number of 0 to 5, preferably 0, 1 or 2, is converted to a compound of the formula (2): $MOSO_2CFXCF_2O(CFXCF_2O)_2CF(CF_2Y)COOM^1$ in which X, Y and n are the same as defined above, and M and $M^1$ independently represent an alkali metal atom or an alkaline earth metal atom, and then a compound of the formula (2) is pyrolyzed at a temperature of 150 to 250° C. to obtain a compound of the formula (3): $ASO_2CFXCF_2O(CFXCF_2O)_nCF=CF_2$ in which A is MO—, a hydroxyl group or a fluorine atom, and X and n are the same as defined above.

7 Claims, 3 Drawing Sheets

PROCESS FOR THE PRODUCING PERFLUOROVINYL ETHERSULFONIC ACID DERIVATIVES AND COPOLYMER OF THE SAME

This application is the national phase under 35 U.S.C. §371 of PCT International Application No. PCT/JP98/01472 which has an International filing date of Mar. 31, 1998, which designated the United States of America.

FIELD OF THE INVENTION

The present invention relates to a process of the preparation of a perfluorovinyl ethersulfonic acid derivative, and a copolymer comprising such a derivative. In particular, the present invention relates to an improved process for synthesizing a perfluorovinyl ethersulfonic acid derivative which can be used as a monomer to prepare a strongly acidic fluorine-containing polymeric electrolyte, and the use of such a derivative as a monomer of a block copolymer.

PRIOR ART

In general, perfluorovinyl ethersulfonic acid derivatives are synthesized according to a reaction path shown in following Scheme 1:

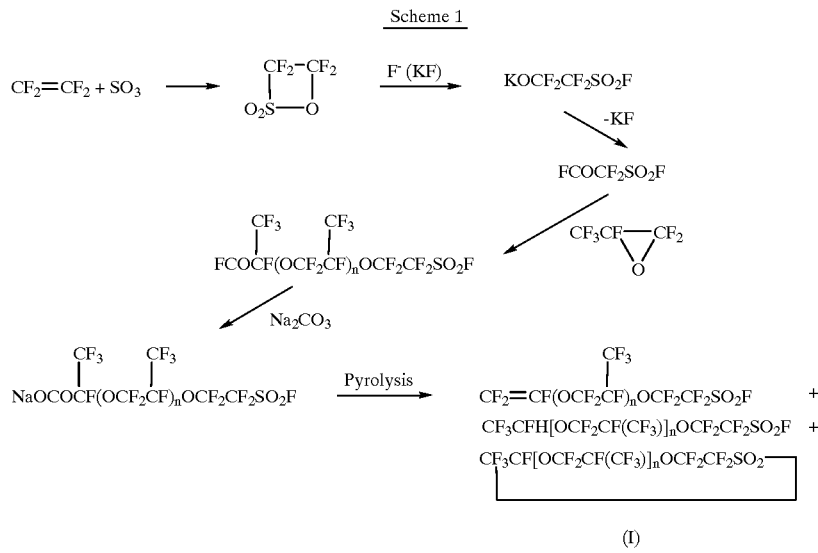

(I)

In the conventional reaction, the intramolecular cyclization of a compound takes place in the final pyrolysis step depending on the number of n (see Scheme 1), and thus, the yield of intended vinyl ethers may decrease, or the cyclization reaction selectively proceeds particularly when n is 0. Therefore, $CF_2=CFOCF_2CF_2SO_2F$ (II) cannot be obtained.

Accordingly, a compound of the formula (I) in which n is 1 or 2 is selected and practically used as a monomer for a sulfonic acid type ionomer.

Carboxylic acid type ionomers are also proposed as such ionomers, and a crystalline copolymer comprising $CF_2=CF[OCF_2CF(CF_3)]_nOCF_2CF_2COOH$ and tetrafluoroethylene is commonly used.

Sulfonic acid type ionomers and carboxylic acid type ionomers have their own advantages and disadvantages, and they have complementary characteristics to each other. It is known that their properties are improved by various methods such as modification or compounding, when they are used in the form of an ion-exchange membrane.

The above compound (II) has a good copolymerizing reactivity with various olefins, and can be easily copolymerized with, in particular, tetrafluoroethylene to give an ionomer having a large ion-exchange capacity. In view of such utility of the compound (II), it has been proposed to synthesize the compound (II) according to the reaction path of following Scheme 2 while avoiding the formation of cyclic compounds in Scheme 1:

Scheme 2

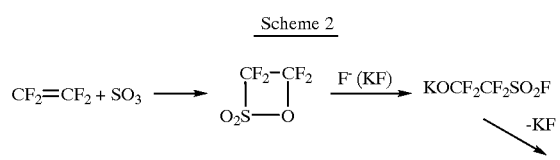

-continued

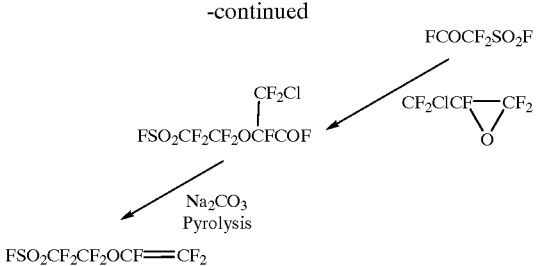

However, this process has a problem that it should use a special chlorine-containing epoxy compound. A method is also known, which comprises ring opening the cyclic compound in Scheme 1 with an alkali metal alcoholate to obtain the compound (II), but no satisfactory result has been attained.

Such known copolymeric ionomers are crystalline and designed so that they are not swelled with or dissolved in water. Thus, it has been believed that copolymers having a high ion-exchange capacity of 600 g/mole or less would have less utility. However, water-soluble amorphous copolymers having a high ion-exchange capacity can be readily obtained, when the compound (II) is used in the form of a water-soluble salt having the formula:

$$CF_2=CFOCF_2CF_2SO_3Na \quad (III)$$

is used and copolymerized with tetrafluoroethylene, trifluoroethylene, vinylidene fluoride, ethylene, etc.

When such amorphous copolymers are further subjected to a living radical polymerization, which is known as "an iodine-transfer polymerization method" (see "KOBUNSHI RONBUNSHU" (Collected Papers on Polymers), Vol. 49, No. 10 (1992) 765–783, and Polymeric Materials Encyclopedia, Vol. 5, 3847–3860 (CRC Press)), to obtain block or graft copolymers with water-insoluble polymers such as copolymers of tetrafluoroethylene with hexafluoropropylene or a perfluoroalkyl vinyl ether (e.g. $CF_2=CFOC_3F_7$), which are known as "FEP" or "PFA", polyvinylidene fluoride, or other fluoropolymers, the obtained polymers become water-insoluble and have a minimum swelling property in water. Accordingly, ionomers having a large ion-exchange capacity of 600 g/mole or less and good mechanical properties can be obtained.

The same measures can be applied to the carboxylic acid type ionomers.

From such a viewpoint, an effective synthesis method of a sulfonic acid derivative having a minimally stable structure such as a compound of the formula (III) is desired to design an ionomer having a large ion-exchange capacity.

SUMMARY OF THE INVENTION

As the result of extensive studies, it has been found that, when a raw material having a —$SO_2F$ group used in the final reaction step in Scheme 1 is once converted to a sulfonate salt (e.g. —$SO_3Na$), completely dried and then pyrolyzed, the raw material can be converted to a desired product while suppressing the cyclization reaction.

Accordingly, the present invention provides a process for the preparation of a vinyl ethersulfonic acid derivative comprising the steps of:

converting a compound of the formula (1):

$$FSO_2CFXCF_2O(CFXCF_2O)_nCF(CF_2Y)COF \quad (1)$$

wherein X is a fluorine atom, a chlorine atom or a trifluoromethyl group, Y is a fluorine atom, a chlorine atom, a bromine atom or an iodine atom, and n is a number of 0 to 5, preferably 0, 1 or 2 to a compound of the formula (2):

$$MOSO_2CFXCF_2O(CFXCF_2O)_nCF(CF_2Y)COOM^1 \quad (2)$$

wherein X, Y and n are the same as defined above, and M and $M^1$ independently represent an alkali metal atom or an alkaline earth metal atom, and pyrolyzing a compound of the formula (2) at a temperature of 150 to 250° C. to obtain a compound of the formula (3):

$$MOSO_2CFXCF_2O(CFXCF_2O)_nCF=CF_2 \quad (3)$$

wherein X, M and n are the same as defined above.

DETAILED DESCRIPTION OF THE INVENTION

Figure 1:
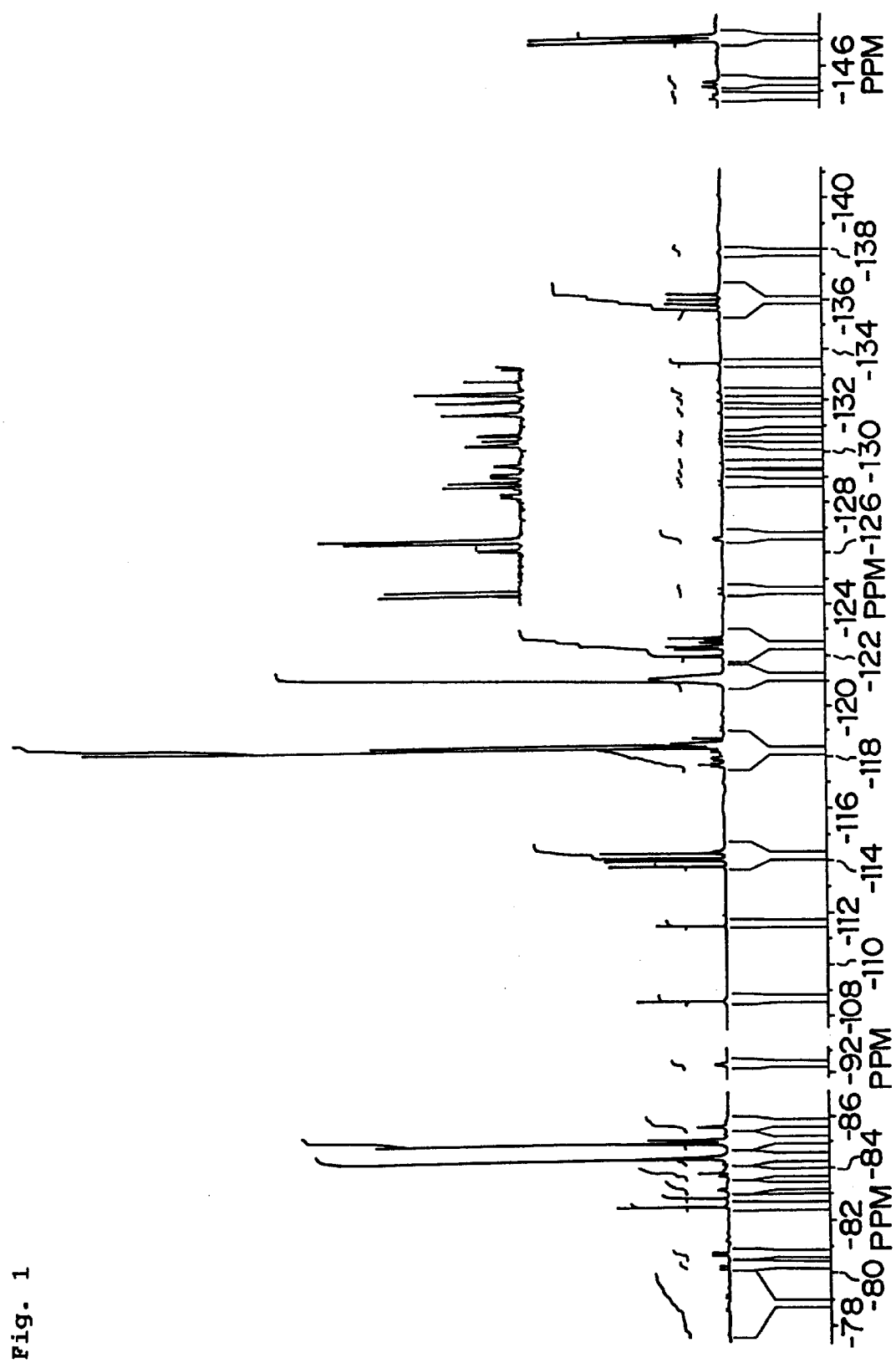
FIG. 1 is the $^{19}$F-NMR spectrum of the aqueous solution of a pyrolyzed product obtained in the step 1.6) of Example 1.

For example, in the case of $FSO_2CF_2CF_2OCF(CF_3)COF$, the $FSO_2$— group does not react with $Na_2CO_3$, and only the —COF group is converted to a —COONa group, when $FSO_2CF_2CF_2OCF(CF_3)COF$ is treated with $Na_2CO_3$ in a glyme according to the conventional method. Thus, when the resulting compound is pyrolyzed, it forms only a cyclic compound (see the bottom of Scheme 1).

According to the present invention, a —COF group is converted to a —COOM group, and also a $FSO_2$— group is converted to a $MOSO_2$ group, using the aqueous or alcoholic solution of the hydroxide of an alkali metal or an alkaline earth metal.

This reaction can be carried out by hydrolyzing or neutralizing a compound of the formula (1) or its ester derivative with the aqueous or alcoholic solution (or dispersion) of the hydroxide of an alkali metal or an alkaline earth metal. When an ester derivative is used, it is necessary to proceed the reaction until the pH of the reaction system reaches 9.

A decarboxylate reaction by pyrolysis in the latter step of the process of the present invention can convert, for example, $NaSO_3CF_2CF_2OCF(CF_3)COONa$ as such to $NaSO_3CF_2CF_2OCF=CF_2$ by solid phase pyrolysis, after the complete drying of $NaSO_3CF_2CF_2OCF(CF_3)COONa$. However, better results are attained, when the decarboxylate reaction is carried out using the dispersion of a starting compound in an inert solvent, since side reactions tend to take place in the solid phase pyrolysis, as can be seen from Scheme 1.

Perfluorinated, perfluorochlorinated, or partially hydrogenated or etherified fluorocarbons can be used as inert solvents. Solvents having a boiling point of 200° C. or higher under atmospheric pressure are preferable, since the reaction can be carried out under atmospheric pressure. Typical examples of such solvents include $Cl(CF_2CFCl)_nCl$ (n=3 or 4), $CF_3[OCF(CF_3)CF_2]_mF$ (m=6 to 8), etc.

The decarboxylate reaction is carried out generally at a temperature of 150° C. or higher, preferably 200° C. or higher. Good results are attained, when the reaction is carried out and terminated in a short time at a temperature of 200° C. or higher.

In a more preferred embodiment, the dispersion of the above salt in an inert solvent is continuously supplied in a tubular reactor kept at a temperature of 200° C. or higher, and the salt is decarboxylated in a certain time. Then, the reaction mixture is removed from the reactor, and the product is isolated from the solvent. The solvent may be recycled.

The preparation method of the present invention is particularly suitable to prepare a compound of the formula (III), that is, in the case of a compound of the formula (I) in which n is 0, while it can be applied to the preparation of a derivative of the formula (2) in which n is 1 or larger.

The process of the present invention provides a vinyl ethersulfonate salt. This salt can be converted to a sulfonyl chloride by the treatment with a phosphorus chloride. Furthermore, this salt can be converted to a sulfonyl fluoride by the treatment with an alkali metal fluoride.

According to the process of the present invention, a vinyl ethersulfonate salt is directly obtained. Thus, this product can be polymerized in an aqueous polymerization method using water as a medium. Alternatively, such a salt is converted to a sulfonyl fluoride, and the sulfonyl fluoride is polymerized by solution, suspension or emulsion polymerization in a fluorocarbon solvent.

A vinyl ethersulfonic acid derivative prepared by the process of the present invention can be readily copolymerized in the presence of a radical polymerization initiator with one or more comonomers such as tetrafluoroethylene, vinylidene fluoride, trifluoroethylene, chlorotrifluoroethylene, ethylene, etc. Furthermore, a vinyl ethersulfonic acid derivative is terpolymerized with one or more of the above comonomers and also hexafluoropropylene, a perfluoro(alkyl vinyl ether), etc. to obtain random copolymers or alternating copolymers as the case may be.

Particularly advantageous copolymers in the present invention are those containing at least 20 mole %, preferably 30 to 50 mole % of a vinyl ethersulfonic acid derivative.

In the first step of the polymerization process of the present invention, the above monomers are supplied in an aqueous solution of an alkali or alkaline earth metal salt preferably containing a vinyl ethersulfonic acid or its ammonium salt, in the presence of a water-soluble radical polymerization initiator such as ammonium persulfate in a necessary amount to initiate polymerization, and a required amount of a perfluoroalkylene diiodide or a perfluoroalkenyl iodide having an unsaturated bond (e.g., $CF_2$=CFI, $CF_2$=$CFOCF_2CF_2I$, etc.), which is used to perform an iodine-transfer polymerization reaction. Such a polymerization method itself is known (see, for example, Collected Papers on Polymers, Vol. 49, No. 10 (1992) 765–783). This polymerization mode is applicable especially to the preparation of water-soluble polymers.

Following the above first step of the polymerization (the polymer segment obtained in the first step being referred to as "Segment A"), the second step of the polymerization is carried out (the polymer segment obtained in the second step being referred to as "Segment B") and thus block copolymers having a structure of B-A-B or A-B, or graft polymers can be obtained.

In the second step of the polymerization, the water-soluble polymer obtained in the first step may be liberated with a strong acid such as hydrochloric acid to remove the effective amount of a vinyl ethersulfonate salt monomer, and the fresh aqueous solution of the polymer is prepared. Then, the above-described monomers are polymerized in the absence of an iodide, unlike the first step. Thereby, a water-insoluble and generally crystalline block copolymer comprising bonded fluororesin segments is obtained. In this case, the prepared block copolymer is recovered in the form of an emulsion or a suspension comprising fine particles.

The molecular weight of the segment A is usually from about 5,000 to about 1,000,000, and can be controlled by the yield of a prepared polymer and the supplied amount of an iodide. The weight ratio of the segment A to the segment B can be arbitrarily selected from a range between 98:2 and 5:95, preferably between 95:5 and 40:60. Consequently, the molecular weight of the whole block polymer is from about 5,000 to about 3,000,000.

In the block polymer of the present invention, a water-insoluble crystalline segment B can be bonded to a segment A by relatively increasing the concentration of one or more monomers other than a vinyl ethersulfonic acid in the second polymerization step after the completion of the first polymerization step, and the change of a monomeric composition can be continuously carried out. Such a structure of a block polymer is called "tapered block". In an actual preparation method, the polymerization is continued while adding a vinyl ethersulfonic acid or reducing the relative concentration of one or more copolymerizable monomers to maintain a constant composition, since the concentration of a vinyl ethersulfonic acid in an aqueous solution decreases as the polymerization proceeds in the first polymerization step. When the latter measure, that is, the decrease of copolymerizable monomers, is employed, the polymerization can be switched from the first polymerization step to the second polymerization step by discontinuously increasing the concentration of one or more copolymerizable monomers after sufficiently decreasing the concentration of the remaining vinyl ethersulfonic acid.

As described above, the present invention provides a process for the easy preparation of a vinyl ethersulfonic acid derivative while suppressing side reactions through a novel reaction route which has not been employed, and thus makes it possible to synthesize an ionomer, which has not been prepared and can achieve good characteristics such as an ion-exchange capacity, electrical resistance, water-resistance, etc. A skilled person in the art can understand that, because of the structural characteristics of a block polymer, such an ionomer has a phase-separated structure, and thus exhibits specific properties such as selective ion permeability, stereospecificity, etc., which are advantageous properties when the ionomer is used as an ion-exchange membrane, a sensor, a selective permeation membrane, a catalyst, a solid electrolyte, and a fuel cell comprising a solid electrolyte.

EXAMPLES

The present invention will be illustrated by the following examples.

Example 1

1.1) $SO_3$ (20 ml), which had been freshly distilled from SULFAN®, was supplied in a 60 ml glass-made pressure autoclave, and the internal atmosphere was replaced and purged with pure nitrogen gas. As soon as tetrafluoroethylene was supplied under pressure, an exothermic reaction started. Then, the reaction was continued while adjusting a temperature in the range between 40° C. and 60° C. and a pressure in the range between 1 kg/cm² and 2 kg/cm². After 40 minutes, the amount of the product increased to 52 ml. When no further tetrafluoroethylene was absorbed, the autoclave was cooled to terminate the reaction. The reaction product was a colorless transparent liquid, and the distillation of the product confirmed that it was substantially pure tetrafluoroethylene-sultone.

1.2) Potassium fluoride (4g), which had been fully dried at 300° C., was charged in a 60 ml glass-made pressure autoclave, and the autoclave was immediately sealed under the stream of nitrogen gas. Then, diglyme (10 ml) was supplied, and the sultone (10 ml), which was obtained in the step 1.1 was gradually dropwise added. A vigorous exothermic reaction started. It was confirmed by $^{19}$F-NMR that the substantially quantitative isomerization of the sultone to $FSO_2CF_2COF$ was completed, while free $FSO_2CF_2CF_2OK$ was also detected.

1.3) Hexafluoropropylene oxide (HFPO) was supplied up to 2 kg/cm²G into the same reactor as used in the step 1.2 containing $FSO_2CF_2COF$, which had been prepared under the same conditions as those in the step 1.2. Immediately, an exothermic reaction started. Then, the reaction was continued for 3 hours while adjusting a temperature in the range between 20° C. and 40° C. and a pressure in the range between 2 kg/cm$^2$ and 1 kg/cm$^2$. After that, the rate of pressure dropping decreased. Thus, the reaction was terminated, and the residual gas was discharged.

The volume of the reaction product was 27 ml, and the reaction product consisted of a yellow upper phase and a colorless lower phase. The distillation of the product confirmed that the most of the product (about 90 vol. %) was $FSO_2CF_2CF_2OCF(CF_3)COF$, which is the mono-adduct of HFPO, while slight amounts of $FSO_2CF_2COF$ and the di-adduct were formed.

1.4) $FSO_2CF_2CF_2OCF(CF_3)COF$ obtained in the step 1.3 was reacted with a large excess amount of methanol, and the product was washed with water, dried, and then distilled. Thus, a methyl ester: $FSO_2CF_2CF_2OCF(CF_3)COOMe$ (boiling point: 72–83° C./760 mmHg) was obtained.

1.5) The ester obtained in the step 1.4 was neutralized with alcoholic sodium hydroxide, and $NaSO_3CF_2CF_2OCF(CF_3)COONa$ was quantitatively obtained. Alcohol and water were thoroughly removed with a rotary evaporator under a reduced pressure, and the residue was ground to obtain a white powder.

1.6) The powder obtained in the step 1.5 (1 g) was charged in a 50 ml flask, and vacuum dried in a nitrogen stream under pressure of 10 mmHg at 100° C. Then, it was heated on an oil bath kept at 230° C. for 20 minutes. FIG. 1 shows the $^{19}$F-NMR spectrum of the aqueous solution of the obtained solid.

Figure 2:
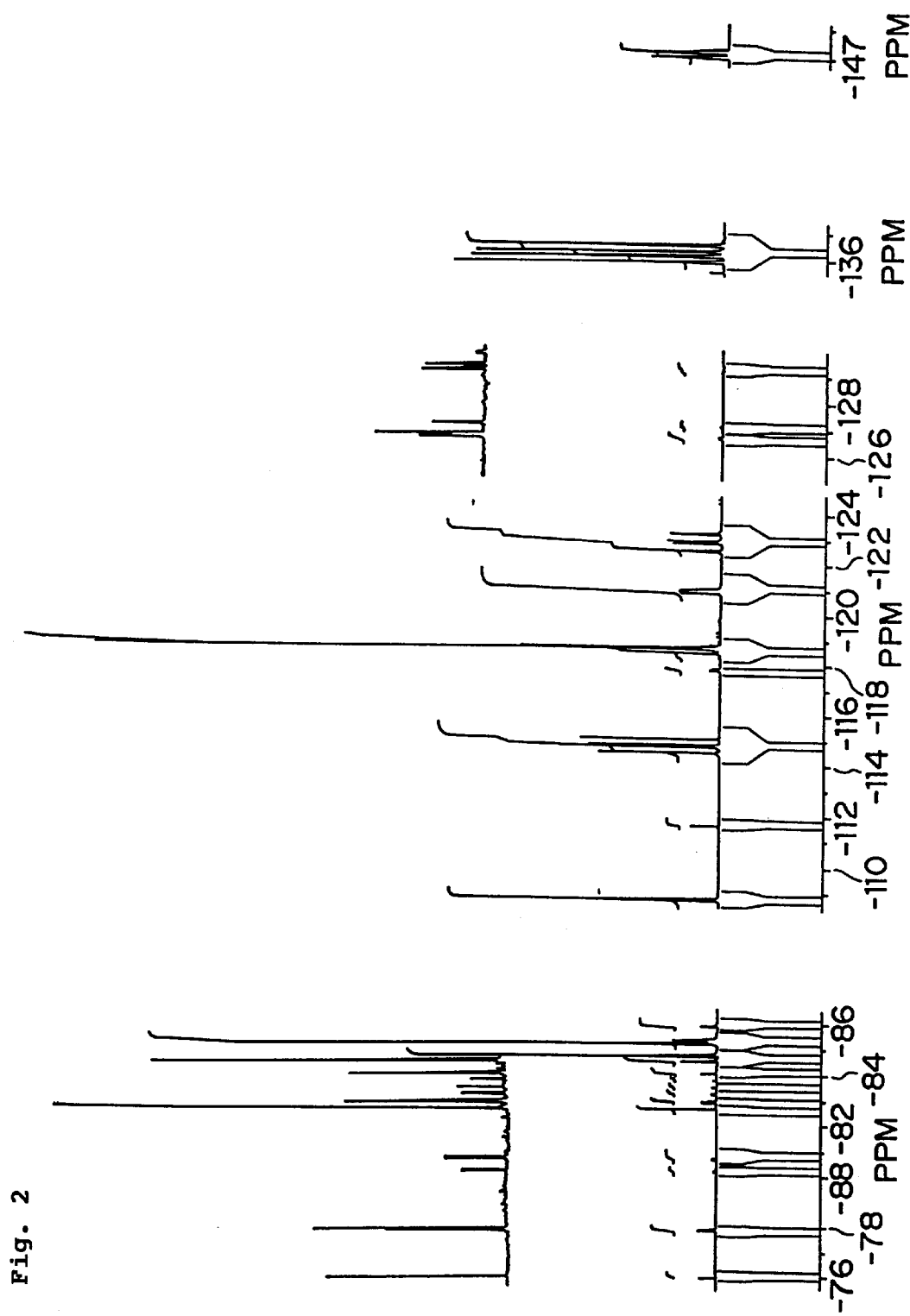
FIG. 2 is the $^{19}$F-NMR spectrum of the aqueous solution of a pyrolyzed product obtained in the step 1.7) of Example 1.

1.7) The powder obtained in the step 1.5 (1 g) was charged in a 50 ml flask, and $Cl(CF_2CFCl)_3Cl$ (5 ml) was added as an inert solvent. The mixture was vacuum dried under the same conditions as those in the step 1.6, and then heated on an oil bath kept at 220° C. for 10 minutes while stirring with a magnetic stirrer. The product was recovered by filtration. FIG. 2 shows the $^{19}$F-NMR spectrum of the aqueous solution of the product.

The product was mainly $NaSO_3CF_2CF_2OCF=CF_2$, while a small amount of $NaSO_3CF_2CF_2OCFHCF_3$ was detected as a by-product.

Figure 3:
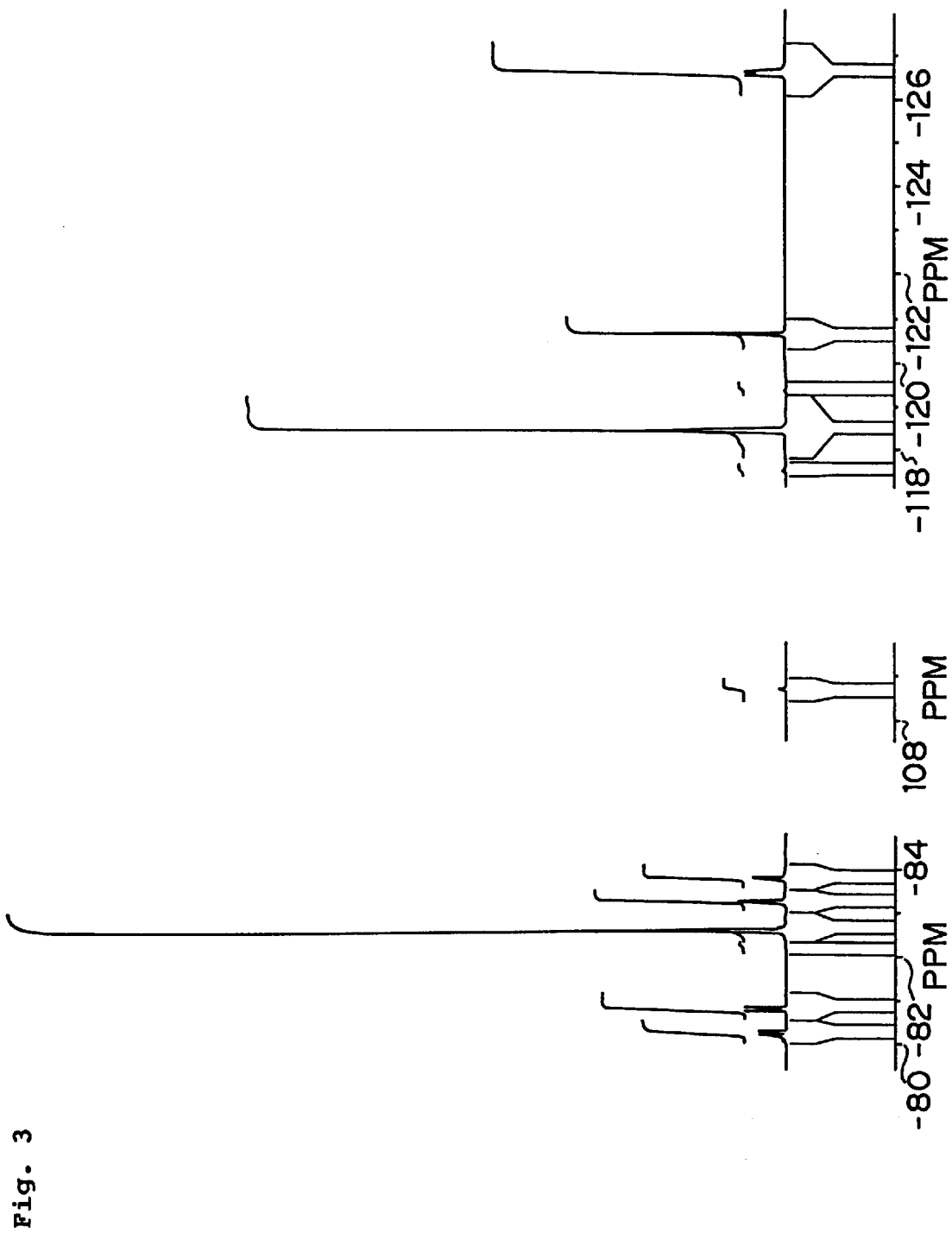
FIG. 3 is the $^{19}$F-NMR spectrum of the aqueous solution of $NaSO_3CF_2CF_2OCF(CF_3)COONa$.

For reference, FIG. 3 shows the $^{19}$F-NMR spectrum of the aqueous solution of $NaSO_3CF_2CF_2OCF(CF_3)COONa$.

From the above results, it can be understood that the heat treatment in an inert solvent is excellent from the viewpoint of a yield.

Example 2

2.1) The powder of $NaSO_3CF_2CF_2OCF=CF_2$, which was prepared in the same manner as that in the step 1.7 of Example 1, was purified by washing with a fluorocarbon solvent (HFC-225), filtration, and recrystallization from isopropanol. Then, the dried product was dissolved in water to obtain a 20 wt. % aqueous solution.

This solution (20 ml), pure water (180 ml) and ammonium persulfate (50 mg) were charged in a 500 ml stainless steel autoclave equipped with a stirrer, and the interior space of the autoclave was thoroughly replaced with nitrogen gas. Thereafter, the autoclave was pressurized to 10 kg/cm$^2$G with tetrafluoroethylene gas, and $I(CF_2)_4I$ (1,4-diiodoperfluorobutane) (0.5 g) was charged in the autoclave under pressure. Then, the mixture was heated to 70° C. while stirring. The pressure started to decrease after 30 minutes from the temperature reaching 70° C. When the pressure decreased to 10 kg/cm$^2$G, tetrafluoroethylene was supplied under pressure to increase the pressure up to 11 kg/cm$^2$G. The reaction was continued for 6.5 hours while repeating the pressure decrease and pressurizing with tetrafluoroethylene gas. Thereafter, the reaction mixture was cooled, and the pressure was released to terminate the polymerization. The product was a colorless, transparent and slightly viscous liquid.

2.2) A 20% aqueous solution of $NaSO_3CF_2CF_2OCF=CF_2$ (20 ml) was added to the product obtained in the step 2.1, and ammonium persulfate (10 mg) was supplemented. Then, the polymerization of tetrafluoroethylene was continued in the same manner as in the step 2.1. After 4 hours, a colorless, transparent and appreciably viscous aqueous solution was obtained.

2.3) In the same autoclave as used in the previous steps, the solution obtained in the step 2.2 (50 ml), pure water (150 ml) and the 20% aqueous solution of $NaSO3CF_2CF_2OCF=CF_2$ (20 ml) were charged, and ammonium persulfate (5 mg) was supplemented. Then, the polymerization of tetrafluoroethylene was continued in the same manner as in the step 2.1 for 7 hours, and the viscous aqueous solution of a polymer was obtained.

When 2N hydrochloric acid was dropwise added to the viscous aqueous solution while stirring, the solution was separated into two phases. After the solution was kept standing, the polymer gel precipitated in the lower phase. The precipitated polymer gel was recovered. Water was added to the recovered polymer gel to form an aqueous solution again, and the polymer was precipitated by the addition of 2N hydrochloric acid. These procedures were repeated one more time (three times in total). The recovered polymer gel was kept standing, and the exuded acid phase was fully removed. Then, the polymer gel was vacuum dried at 100° C. to obtain a mass of an ionomer (7 g), which was in a solid state at room temperature.

The neutralization titration confirmed that the copolymer contained 41 mole % of the vinyl ethersulfonic acid. The molecular weight of the copolymer was about 110,000 when it was calculated from the measured iodine value.

2.4) The ionomer (5 g) obtained in the step 2.3 was dissolved in pure water (30 ml), and ammonium persulfate (5 mg) was added to the solution. Then, the solution was charged in a 60 ml glass-made pressure autoclave equipped with a stirrer. After thoroughly deoxidizing the interior of the system, a perfluorovinyl ether ($CF_2=CFOC_3F_7$) (3 g) was injected, and then the autoclave was pressurized with tetrafluoroethylene up to 10 kg/cm$^2$G. Thereafter, the mixture was heated up to 70° C. while stirring, and immediately the pressure started to drop. The polymerization was terminated when the mixture became white turbid by the visual inspection, and thus a dispersion containing a slight amount of precipitates was obtained.

When the dispersion was treated with 2N hydrochloric acid, a white muddy precipitate formed. The precipitate was sufficiently washed with water to remove the white turbid water-soluble material. Then, the water-insoluble material was dried at 100° C. for 12 hours to obtain white particles (6.5 g).

The particles had an endothermic peak at 275° C., when it was analyzed with a differential scanning calorimeter (DSC). When the particles were heat pressed at 280° C., a slightly pink transparent sheet was obtained. This sheet was not dissolved in water, or hardly swelled with water. When it is dipped in 2N hydrochloric acid, it can easily be converted to a —SO$_3$H type sheet. Furthermore, when it is dipped in an aqueous solution of sodium hydroxide, it can easily be converted to a —SO$_3$Na type sheet.

The backbone of this polymer was assumed to be an A-B-A block polymer from the principle of the iodine-transfer polymerization (A being a crystalline random copolymer segment of tetrafluoroethylene and a perfluorovinyl ether, and B being an amorphous random copolymer segment of tetrafluoroethylene and a vinyl ethersulfonic acid).

What is claimed is:

1. A process for preparing a vinyl ethersulfonic acid derivative comprising the steps of:

converting a compound of formula (1):

$$FSO_2CFXCF_2O(CFXCF_2O)_nCF(CF_2Y)COF \qquad (1)$$

wherein X is a fluorine atom, a chlorine atom or a trifluorometyl group, Y is a fluorine atom, a chlorine atom a bromine atom or an iodine atom, and n is a number of 0 to 5, to a compound of formula (2):

$$MOSO_2CFXCF_2O(CFXCF_2O)_nCF(CF_2Y)COOM^1 \qquad (2)$$

wherein X, Y and n are the same as defined above, and M and M$^1$ independently represent an alkali metal or an alkaline earth metal atom, and pyrolizing a compound of the formula (2) at a temperature of 150 to 250° C. to obtain a compound of formula (3):

$$MOSO_2CFXCF_2O(CFXCF_2O)_nCF=CF_2 \qquad (3)$$

wherein X, M and n are the same as defined above.

2. A process according to claim 1, wherein n is 0, 1 or 2.

3. A process according to claim 1, wherein said pyrolysis is carried out in the presence of an inert solvent.

4. A process according to claim 1, wherein a vinyl ethersulfonic acid derivative of the formula (4):

$$ASO_2CF_2CF_2OCF=CF_2 \qquad (4)$$

wherein A is a group: —OM in which M is an alkali metal or an alkaline earth metal atom, a hydroxyl group or a fluorine atom using a compound of the formula (I) in which X is a fluorine atom, n is 0 and Y is a fluorine atom, as a starting compound.

5. A process for preparing a block polymer comprising the steps of:

copolymerizing a vinyl ethersulfonic acid derivative of the formula (3):

$$ASO_2CFXCF_2O(CFXCF_2O)_nCF=CF_2 \qquad (3)$$

wherein X is a fluorine atom, A is a group —OM in which M is an alkali metal or an alkaline earth metal atom, a hydroxyl group or a fluorine atom with at least one monomer selected from the group consisting of fluoroolefins and olefins in the presence of a polymerization initiator and perfluoroalkylene diiodide to obtain a copolymer, and copolymerizing at least one monomer selected from the group consisting of fluoroolefins and olefins in the presence of the copolymer obtained in the previous step.

6. A block copolymer which is prepared by a process as claimed in claim 5 and has a molecular weight of 5×10$^3$ to 3×10$^6$.

7. A process according to claim 1, wherein the compound of formula 1 is converted to the compound of formula (2) by using an aqueous or alcoholic solution of hydroxide of an alkaline earth metal.

* * * * *